(12) United States Patent
Asaoka et al.

(10) Patent No.: US 6,737,069 B1
(45) Date of Patent: May 18, 2004

(54) COSMETIC COMPOSITIONS CONTAINING AMPHOTERIC POLYURETHANES

(75) Inventors: Seiji Asaoka, Suita (JP); Katsuya Koyama, Itami (JP); Toshitaka Tsuzuki, Minoo (JP); Tomohiro Hashimoto, Kawanishi (JP)

(73) Assignee: National Starch and Chemical Investment Holding Corporation, New Castle, DE (US)

( * ) Notice: Subject to any disclaimer, the term of this patent is extended or adjusted under 35 U.S.C. 154(b) by 87 days.

(21) Appl. No.: 10/049,361

(22) PCT Filed: Aug. 10, 2000

(86) PCT No.: PCT/US00/21874
§ 371 (c)(1),
(2), (4) Date: Feb. 6, 2002

(87) PCT Pub. No.: WO01/10394
PCT Pub. Date: Feb. 15, 2001

(30) Foreign Application Priority Data

Aug. 10, 1999 (JP) ............................................. 11-226559

(51) Int. Cl.$^7$ ................................................. A61K 6/00
(52) U.S. Cl. .................... 424/401; 424/70.1; 424/70.12; 424/70.21; 528/61; 528/65
(58) Field of Search ................................. 424/401, 70.1, 424/70, 70.17, 70.21; 528/61, 65

(56) References Cited

U.S. PATENT DOCUMENTS 5,100,658 A * 3/1992 Bolich, Jr. .................... 424/70
6,335,003 B1 * 1/2002 Kim et al. ................. 424/70.17

FOREIGN PATENT DOCUMENTS

| EP | 0 619 111 B1 | 12/1996 |
| EP | 0 925 778 B1 | 7/2001 |
| WO | 99/39688 | 8/1999 |
| WO | 00/12056 | 3/2000 |

OTHER PUBLICATIONS

JP H10–27595 (English abstract only), Application pending in Japan filed on Feb. 9, 1998.

* cited by examiner

Primary Examiner—Thurman K. Page
Assistant Examiner—Lakshmi Channavajjala
(74) Attorney, Agent, or Firm—Karen G. Kaiser

(57) ABSTRACT

The present invention provides a cosmetic which is superior in both characteristics of feel and spread at the time of application. The cosmetic is a cosmetic comprising an amphoteric urethane resin having carboxyl group(s) and tertiary amino group(s) in a molecule, and a silicone polymer.

14 Claims, No Drawings

COSMETIC COMPOSITIONS CONTAINING AMPHOTERIC POLYURETHANES

FIELD OF THE INVENTION

The present invention relates to cosmetics containing an amphoteric urethane resin and a silicone polymer.

DESCRIPTION OF THE RELATED ART

As a base resin for cosmetics such as hair fixatives, for example, water-soluble resins such as nonionic (non-ionic) polyvinyl pyrrolidone (PVP), cationic acrylic resin or cellulose, anionic acrylic resin or polyvinyl acetate, and amphoteric acrylic resin or polyvinyl acetate have hitherto been used. Hair fixatives comprising these water-soluble resins as the base resin have merits such as high curl holding power and excellent durability, but have problems such as poor touch, which is important for cosmetics, and drastically poor feel.

On the other hand, the present inventors found that an amphoteric urethane resin having carboxyl group(s) and tertiary amino group(s) in a molecule can provide excellent feel because of the elasticity and strong toughness of the urethane resin and filed a patent application with respect to a resin composition for cosmetics, comprising the amphoteric urethane resin as the base resin (Japanese Patent Application No Hei 10-27595).

However, the cosmetic comprising the amphoteric urethane resin as the base resin is superior in feel, but has such a problem that a friction coefficient of the surface is large and spread at the time of application is inferior because of poor surface smoothness.

SUMMARY OF THE INVENTION

The present invention has been accomplished under these circumstances and an object thereof is to provide a cosmetic which is superior in both characteristics of touch and spread at the time of application.

To attain the object described above, the present invention is directed to a cosmetic comprising an amphoteric urethane resin having carboxyl group(s) and tertiary amino group(s) in a molecule, and a silicone polymer.

The present inventors have studied intensively to solve the problems such as surface smoothness, which is a weak point in case of using the amphoteric urethane resin. As a result, they have found that, when using an amphoteric urethane resin in combination with a silicone polymer, good results are obtained. That is, since the compatibility of the said amphoteric urethane resin with the silicone polymer is not high and the silicone polymer has stronger hydrophobicity, the amphoteric urethane resin and silicone polymer cause micro phase separation and the silicone polymer is unevenly distributed on the surface, thereby making it possible to provide the surface with the smoothness. As a result, they have found that a cosmetic comprising the amphoteric urethane resin in combination with the silicone polymer is superior in spread at the time of application without impairing the touch when using the amphoteric urethane resin alone, thus completing the present invention.

When using an aqueous solution or a water dispersion of the silicone polymer as the silicone polymer, the compatibility with the amphoteric urethane resin is enhanced to some degree, thereby making it possible to prepare a cosmetic having good stability.

When a structural unit derived from ethylene oxide is introduced, as a nonionic hydrophilic component, into the structure of the amphoteric urethane resin, sufficient hydrophilicity can be obtained and the hair washability is particularly improved when using as a hair cosmetic.

By introducing polysiloxane bond(s) into the structure of the said amphoteric urethane resin, the touch is further improved when using as a hair cosmetic.

DESCRIPTION OF THE PREFERRED EMBODIMENTS

The embodiments of the present invention will now be described below.

The cosmetics of the present invention can be obtained by using an amphoteric urethane resin having carboxyl group(s) and tertiary amino group(s) in a molecule, and a silicone polymer.

The cosmetics of the present invention are used as hair cosmetics such as foam hair fixative, gel-like hair fixative, aerosol spray hair fixative, pump spray hair fixative and creamy hair fixative; skin care cosmetics such as shaving cream, skin care lotion and sunscreen lotion; and make-up cosmetics such as nail polish, mascara and foundation; and are particularly preferably used as hair cosmetics.

The amphoteric urethane resin having carboxyl group(s) and tertiary amino group(s) in a molecule can be prepared, for example, by reacting a polyol compound (component A), a polyisocyanate compound (component B) and a compound having active hydrogens) and carboxyl group(s) (component C) in the presence of excess isocyanate groups to form an isocyanate group-containing prepolymer, and reacting the isocyanate group-containing prepolymer with a compound having active hydrogen(s) and tertiary amino group(s) (component D). Alternatively, the amphoteric urethane resin can also be prepared by replacing the sequence of the reaction between the above specific components C and D, that is, by reacting the above components A, B. and D in the presence of excess isocyanate groups to form an isocyanate group-containing prepolymer, and reacting the isocyanate group-containing prepolymer with the above specific component C. Such a method makes it possible to prepare an amphoteric urethane resin simply and safely as compared with a conventional method. In the above preparation method, when both specific components C and D are simultaneously reacted, together with the components A and B, the carboxyl group(s) in the component C and the tertiary amino group(s) in the component D form(s) a salt, which is insoluble in the reaction system. As a result, the reaction with the isocyanate compound does not occur even in the presence of the OH group(s), thereby making it impossible to prepare a desired amphoteric urethane resin.

The above polyol compound (component A) is not specifically limited as far as it can be used in the preparation of a normal polyurethane, and examples thereof include polyester poylol, polyether polyol, polycarbonate polyol, polybutadiene polyol, polyisoprene polyol, polyolefin polyol and polyacrylate polyol etc. These polyol compounds are used alone or in combination. Among these polyol compounds, polyester poylol and polyether polyol are preferably used.

Examples of the polyester polyol include those obtained by polycondensing at least one of dicarboxylic acids such as succinic acid glutaric acid, adipic acid, sebacic acid, azelaic acid, maleic acid, fumaric acid, phthalic acid and terephthalic acid with at least one of polyhydric alcohols such as ethylene glyol, propylene glycol, 1,4-butanediol, 1,3-butanediol, 1,6-hexanediol, neopentyl glycol, 1,8- octanediol, 1,10-decanediol, diethylene glycol, spiro-glycol and trimethylolpropane, etc., and those obtained by the ring-opening polymerization of lactones.

Example of the polyether polyol include polyhydric alcohols used in the synthesis of the said polyester polyols, phenols such as bisphenol A, or those obtained by the ring-opening addition polymerization of primary amines or secondary amines and cyclic ether such as ethylene oxide, propylene oxide, oxetane and tetrahydrofuran. Examples thereof include polyoxyethylene polyol, polyoxypropylene polyol, polyoxytetramethylene polyol, and those obtained by the ring-opening addition polymerization of bisphenol A and at least one of propylene oxide and ethylene oxide, etc. (in case of a copolymer it may be either a block copolymer or a random copolymer).

The polyisocyanate compound (component B) is not specifically limited, and examples thereof include organic diisocyanate compounds such as aliphatic diisocyanate compound, alicyclic diisocyanate compound and aromatic diisocyanate compound. These compounds may be used alone or in combination.

Example of the aliphatic diisocyanate compound includes ethylene diisocyanate, 2,2,4-trimethylhexa-methylene diisocyanate, 1,6-hexamethylene diisocyanate, etc. Examples of the alicyclic diisocyanate compound includes hydrogenated 4,4'-diphenylmethane diisocyanate, 1,4-cyclohexane diisocyanate, methylcyclohexylene diisocyanate, isophorone diisocyanate and norbornane diisocyanate, etc. Examples of the aromatic diisocyanate compound includes 4,4'-diphenylmethane diisocyanate, xylylene diisocyanate, toluene diisocyanate and naphthalene diisocyanate, etc. Among these compounds, 1,6-hexamethylene diisocyanate, isophorone diisocyanate, norbornane diisocyanate, etc. are preferable because of the excellent light resistance and low price.

The compound (component C) having active hydrogen(s) and carboxyl group(s) is not specifically limited as far as it is a compound having at least one active hydrogen and at least one carboxyl group in a molecule, and examples thereof include dimethylolpropionic acid (DMPA), dimethylolbutanoic acid, carboxyl group-containing polycaprolactone diol, etc. These compounds may be used alone or in combination.

The compound (component D) having the above active hydrogen(s) and tertiary amino group(s) is not specifically limited as far as it is a compound having at least one active hydrogen and at least one tertiary amino group in a molecule, and examples thereof include N-alkyldialkanolamine compound such as N-methyidiethanolamine and N-butylidiethanolamine, and dimethylaminoethanol, etc. These compounds may be used alone or in combination.

In the production of an isocyanate group-containing prepolymer by using the above respective components, chain extenders or molecular weight inhibitors can be used for the purpose of controlling various characteristics of the amphoteric urethane resin as a final product.

The chain extender is not specifically limited and examples thereof include low-molecular polyol, amines, etc. Examples of the low-molecular polyol includes glycols such as ethylene glycol, propylene glycol, 1,4-butanediol, diethylene glycol, 1,6-hexanediol, spiro-glycol, cyclohexyl dimethanol, hydrogenated bisphenol A, neopentyl glycol, bis(beta-hydroxyethoxy)benzene, and xylylene glycol; and triol such as trimethylolpropane and glycerin. Examples of the amines include ethylenediamine, propylenediamine, piperazine, hydrazine, isophoronediamine methylene(bis-o-chloroaniline) and propylene glycol having amino groups at both ends, etc.

Examples of the molecular weight inhibitor includes propylene glycol having an amino group at one end, etc.

In the production of the amphoteric urethane resin, solvents can be used as needed. For example, organic solvents capable of dissolving both raw materials and polyurethane to be prepared are preferably used. Examples of the organic solvent includes amides such as N-methylpyrrolidone, dimethylformamide and dimethylacetamide; ketones such as acetone and methyl ethyl ketone; esters such as ethyl acetate; cellosolve acetate, cellosolve ether, etc.

In the production of the amphoteric urethane resin, the dispersibility in water can be provided by neutralizing the carboxyl group(s) or tertiary amino group(s) incorporated into the molecule with a neutralizing agent. Examples of the neutralizing agent for the said carboxyl group(s) includes triethylamine, trimethylamine, 2-amino-2-methyl-1-propanol, triethanolamine, potassium hydroxide, sodium hydroxide, etc. Examples of the nutralizing agent for the said tertiary amino group(s) include acetic acid, hydrochloric acid, sulfuric, nitric acid and dimethylsulfuric acid, etc.

In the production of the amphoteric urethane resin, polymerization catalysts known in the field of polyurethane can be used, and examples thereof include tertiary amine catalyst, organometallic catalyst, etc. Examples of the tertiary amine catalyst includes [2,2,2]diazabicyclooctane (DABCO), tetramethylene-iamine, N-methyl morphorine and diazabicycloundecene (DBU), etc. Examples of the organometallic catalyst includes dibutyltin dilaurate, etc.

As the amphoteric urethane resin, in view of the hair washability, those having structural unit(s) derived from ethylene oxide (EO) in the structure are preferably used.

Examples of the structural unit derived from the said EO includes EO unit represented by the general formula (I) described below, propylene oxide (hereinafter abreviated to "PO") unit represented by the general formula (II) described below, etc., and the EO unit is preferably used.

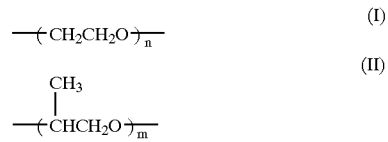

The above amphoteric urethane resin may have both EO and PO units. A proportion of the EO unit to the PO unit is preferably within a range from 10/10 to 2/8, and particularly preferably from 10/0 to 4/6, on a weight basis.

The repeating number n of the EO unit in the general formula (I) is preferably set within a range from 3 to 300, and particularly preferably from 20 to 120. When the n is less than 3, sufficient hydrophilicity can not be provided because of too small amount of the EO unit(s) to be incorporated into the amphoteric urethane resin and, therefore, sufficient hair washability are not likely to be obtained. On the other hand, when n exceeds 300, an adverse influence is likely to be exerted on the moisture resistance or the like because of too strong hydrophilicity of the amphoteric urethane resin. Furthermore, the repeating number m of the PO unit in the general formula (II) is preferably set within a range from 3 to 300, and particularly preferably from 20 to 120. When the amphoteric urethane resin has both EO and PO units, (n+m) is preferably set within a range from 3 to 300, and particularly preferably from 20 to 120.

The amphoteric urethane resin having structural unit(s) derived from ethylene oxide (EO) can be prepared, for example, by reacting a polyol compound (component A), a polyisocyanate compound (component B), a polyethylene oxide derivatives having active hydrogen(s), and a compound having active hydrogen(s) and carboxyl group(s) (component C) in the presence of excess isocyanate groups to form an isocyanate group-containing prepolymer, and reacting the isocyanate group-containing prepolymer with a compound having active hydrogen(s) and tertiary amino group(s) (component D). Alternatively, the amphoteric urethane resin can also be prepared by replacing the sequence of the reaction between the above components C and D. As the above components A to D, the same compounds as those described above can be used.

Examples of the polyethylene oxide derivative having active hydrogen(s) to be used together with the above components A to D is not specifically limited as far as it is capable of introducing a structural unit derived from ethylene oxide (EO) into the structure of the above amphoteric urethane resin, and examples thereof include polyoxyethylene glycol (PEG), polyoxyethylene polyoxypropylene glycol (EOPO block copolymer), etc. Among these, polyoxyethylene glycol is preferably used. The above polyoxyethylene oxide derivative may be any of a type wherein an OH group is introduced at both ends, a type wherein an $NH_2$ group is introduced at both ends, a type wherein an OH group is introduced at one end, and a type wherein an $NH_2$ group is introduced at one end. When using the type wherein an OH group is introduced at both ends or a type wherein an $NH_2$ group is introduced at both ends, an amphoteric urethane resin having the EO unit(s) in a principal chain is obtained. When using the type wherein an OH group is introduced at one end or a type wherein an $NH_2$ group is introduced at one end, an amphoteric urethane resin having EO unit(s) at its side chain(s) or end(s) is obtained.

The molecular weight of the specific polyethylene oxide derivative is preferably within a range from 200 to 20000, and particularly preferably from 1000 to 10000.

To further improve the feel, those having polysiloxane bond(s) in the structure are preferably used as the amphoteric urethane resin.

The repeating number n of a siloxane bond (Si—O) is preferably within a range from 5 to 300, and particularly preferably from 20 to 150. When n is less than 5, it becomes difficult to obtain the sufficient effect on the touch, coming properties, etc. obtained intrinsically by introducing the polysiloxane bond(s) because of too small amount of the polysiloxane bond(s) in the resulting amphoteric urethane resin. On the other hand, when n exceeds 300, the compatibility with other raw materials become inferior because of high hydrophobicity, thereby making it difficult to react them. Furthermore, the adhesion to hair is likely to be inhibited because of too high hydrophobicity of the resulting polymer.

The amphoteric urethane resin having the said polysiloxane bond(s) can be prepared, for example, by reacting a polyol compound (component A), a polyisocyanate compound (component B), a polysiloxane compound having active hydrogen(s) and a compound having active hydrogen(s), and carboxyl group(s) (component C) in the presence of excess isocyanate groups to form an isocyanate group-containing prepolymer, and reacting the isocyanate group-containing prepolymer with a compound having active hydrogen(s) and tertiary amino group(s) (component D). Alternatively, the amphoteric urethane resin can also be prepared by replacing the sequence of the reaction between the above components C and D. As the above components A to D, the same compounds as those described above can be used.

The polysilOxane compound having active hydrogen(s) to be used together with the above components A to D is not specifically limited as far as it is capable of introducing polysiloxane bond(s) into the structure of the amphoteric urethane resin, and examples thereof include polydialkylsiloxanediol, polydialkyl-siloxanemonool, polydialkylsiloxanediamine, polydialkyl-siloxanemonoamine, etc. These compounds may be used alone or in combination. The alkyl group(s) to be combined with Si of the respective siloxane bonds of the said polydialkylsiloxanediol preferably has 1 to 10 carbon atoms, and particularly preferably 1 to 5 carbon atoms. The above polysiloxane compound may contain various siloxane bonds wherein the number of carbon atoms of the alkyl group(s) to be combined with Si of the siloxane bonds varies. Specific examples of the polydialkyl-siloxanediol include polydimethylsiloxanediol, polymethyl-ethylsiloxanediol, etc. Examples of the polydialkyl-siloxanemonool include polydimethyl-siloxanemonool, polymethylethyl-siloxanemonool, etc. Examples of the polydialkylsiloxanediamine include polydimethylsiloxane-diamine, polymethylethyl-siloxanediamine, etc. Examples of the polydialkyl-siloxanemonoamine include poly-dimethylsiloxane-monoamine, polymethylethylsiloxane-monomaine, etc.

Examples of the polysiloxane compound include a type wherein an OH group is introduced at both ends, a type wherein an $NH_2$ group is introduced at both ends, a type wherein an OH group is introduced at one end and a type wherein an $NH_2$ group is introduced at one end. When using the type wherein an OH group is introduced at both ends or a type wherein an $NH_2$ group is introduced at both ends, an amphoteric urethane resin having polysiloxane bond(s) in a principal chain is obtained. When using the type wherein an OH group is introduced at one end or a type wherein an $NH_2$ group is introduced at one end, an amphoteric urethane resin having polysiloxane bond(s) at its side chain(s) or end(s) is obtained.

In the cosmetics of the present invention, the amphoteric urethane resin is preferably used in the form of an aqueous solution. In the present invention, the aqueous solution includes not only an aqueous solution state where the amphoteric urethane resin is completely dissolved in water but also a water dispersion state where the amphoteric urethane resin is dispersed in water.

It is also possible to add a crosslinking agent such as silane coupling agent to the water dispersion of the above amphoteric resin, thereby to provide the crosslinkability. To provide the storage stability, various additives may be added and examples thereof include protective colloidal agents, bactericides, mildewproofing agents, etc.

The silicone polymer used together with the said amphoteric urethane resin is not specifically limited as far as it has polysiloxane bond(s) in a molecule and can be used in cosmetics, and examples thereof include silicone resin, silicone oil, silicone emulsion, silicone rubber, etc. Examples of the silicone rubber include nonionic, polyether-modified, phenyl-modified, amino-modified, alkyl-modified, alkoxy-modified, cyclic silicone polymers, etc. These silicone polymers can be used alone or in combination.

Examples of the nonionic silicone polymer includes those represented by the following general formula (1):

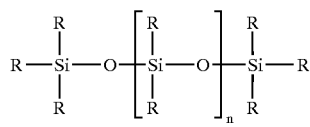

(1)

[wherein R represents a hydrogen atom, hydrocarbon group(s) having 1 to 12 carbon atoms, or —OSi(CH$_3$)$_3$ and may be the same or different; and n represents a numeral of 3 or more].

In the general formula (1), the hydrocarbon group(s) having 1 to 12 carbon atoms is are straight-chain or branched-chain saturated hydrocarbon group(s) and is/are preferably methyl group(s), while n is preferably from 50 to 3000.

Examples of the nonionic silicone polymer represented by the general formula (1) include methyl polysiloxane whose R is entirely methyl group(s).

Examples of the polyether-modified silicone polymer includes those represented by the following general formula (2). Each repeating unit in the silicone polymer of the present invention may be in any form of polymerization such as random polymerization and block polymerization.

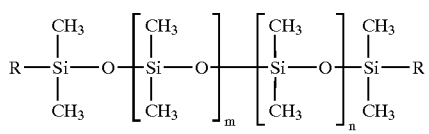

(2)

[wherein R represents hydrocarbon group(s) having 1 to 12 carbon atoms or group(s) represented by the following general formula (2') and may be the same or different, provided that at least one of R(s) is group(s) represented by the following general formula (2'); m represents 0 or a numeral of 1 or more; and n represents a numeral of 1 or more]

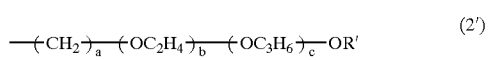

(2')

(wherein R' represents a hydrogen atom or hydrocarbon group(s) having 1 to 10 carbon atoms; a represents a numeral of 1 to 10; b represents a numeral of 1 to 300; and c represents a numeral of 0 to 300)

In the general formula (2), the hydrocarbon group(s) having 1 to 12 carbon atoms represented by R include(s) a straight-chain or branched-chain saturated hydrocarbon group(s), m is preferably from 10 to 500, and n is preferably from 1 to 500. In the general formula (2'), a is preferably 2 to 4, b is preferably from 2 to 50, and c is preferably from 0 to 5.

Examples of the phenyl-modified silicone polymer includes those represented by the following general formula (3):

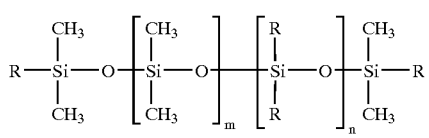

(3)

[wherein R represents hydrocarbon group(s) having 1 to 12 carbon atoms, —OSi(CH$_3$)$_3$ or phenyl group(s) and may be the same or different, provided that at least one of R(s) is phenyl group(s); m represents 0 or a numeral of 1 or more; and n represents a numeral of 1 or more].

In the general formula (3), the hydrocarbon group(s) having 1 to 12 carbon atoms represented by R include(s) straight-chain or branched-chain saturated hydrocarbon group(s), m is preferably from 0 to 500, and n is preferably from 1 to 2000.

As the phenyl-modified silicone polymer represented by the general formula (3) methylphenyl polysiloxane is preferably used.

Examples of the amino-modified silicone polymer includes those represented by the following general formula (4):

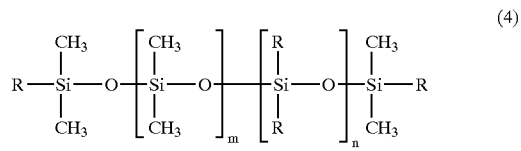

(4)

[wherein R represents a hydrogen atom, hydrocarbon group(s) having 1 to 12 carbon atoms, hydroxyl group(s), methoxy group(s) or group(s) represented by the following general formula (4') or (4") and may be the same or different, provided that at least one of R(s) is group(s) represented by the following general formula (4') or (4"); m represents 0 or a numeral of 1 or more; and n represents a numeral of 1 or more

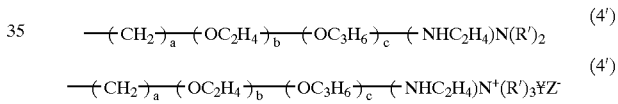

(4')

(4')

[wherein R' represents a hydrogen atom or hydrocarbon group(s) having 1 to 6 carbon atoms and may be the same or different; Z represents a halogen ion or an organic anion; a represents a numeral of 1 to 6; b represents a numeral of 0 to 6; and c represents a numeral of 0 to 6)].

In the general formula (4), the hydrocarbon group(s) having 1 to 12 carbon atoms represented by R include(s) straight-chain or branched-chain saturated hydrocarbon group(s), m is preferably from 3 to 500, and n is preferably from 1 to 500. In the general formulas (4') and (4"), the hydrocarbon group(s) having 1 to 6 carbon atoms represented by R' include(s) straight-chain or branched-chain saturated hydrocarbon group(s).

As the amino-modified silicone polymer represented by the said general formula (4), aminodimethycone represented by the following structural formula is preferably used.

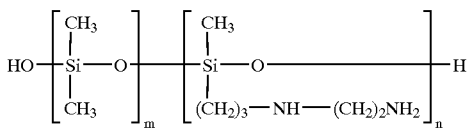

[wherein m and n are as defined in the general formula (4)]

Examples of the alkyl-modified silicone polymer include, those represented by the following general formula (5):

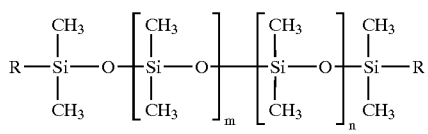

(5)

[wherein R represents hydrocarbon group(s) having 1 to 50 carbon atoms and may be the same or different, provided that at least one of R(s) is hydrocarbon group(s) having 12 to 50 carbon atoms; m represents 0 or a numeral of 1 or more; and n represents a numeral of 1 or more].

In the general formula (5), the hydrocarbon group(s) having 1 to 50 carbon atoms represented by R include(s) straight-chain or branched-chain saturated hydrocarbon group(s), and hydrocarbon group(s) having. 12 to 50 carbon atoms is/are preferably used, and hydrocarbon group(s) having 15 to 40 carbon atoms is/are more preferably used. m is preferably from 10 to 500, and n is preferably from 10 to 500.

Examples of the alkoxy-modified silicone polymer include those represented by the following general formula (6):

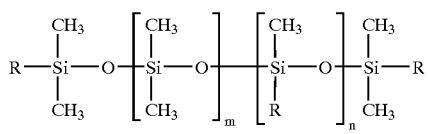

(6)

[wherein R represents hydrocarbon group(s) having 1 to 12 carbon atoms or alkoxy group(s) having 1 to 50 carbon atoms and may be the same or different, provided that at least one of R(s) is alkoxy group(s) having 1 to 50 carbon atoms m represents 0 or a numeral of 1 or more, and n represents a numeral of 1 or more].

In the general formula (6), the hydrocarbon group(s) having 1 to 12 carbon atoms represented by R include(s) straight-chain or branched-chain saturated hydrocarbon group(s). The alkoxy group(s) having 1 to 50 carbon atoms represented by R include(s) straight-chain or branched-chain saturated alkoxy group(s) and alkoxy group(s) having 1 to 20 carbon atoms is/are preferably used. m is preferably from 3 to 500, and n is preferably from 1 to 100.

Examples of the cyclic silicone polymer includes those represented by the following general formula (7):

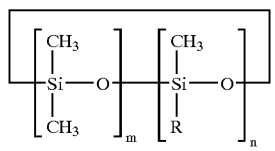

(7)

[wherein R represents hydrocarbon group(s) having 1 to 12 carbon atoms and may be the same or different in each repeating unit; m represents 0 or a numeral of 1 or more; n represents a numeral of 1 or more; and m+n is from 4 to 10].

In the general formula (7), the hydrocarbon group(s) having 1 to 12 carbon atoms represented by R include(s) straight-chain or branched-chain saturated hydrocarbon group(s).

The average molecular weight of these silicone polymers is preferably within a range from 100 to 10,000,000, and particularly preferably from 10,000 to 1,000,000.

The silicone polymer is preferably used in the form of an aqueous solution or a water dispersion in view of the stability for cosmetics The incorporation ratio of the amphoteric urethane resin to the silicone polymer is preferably within a range from 0.1/100 to 100/0.01, and particularly preferably from 100/0.01 to 100/5, in terms of a weight ratio.

Furthermore, any components used commonly in cosmetics such as pigments, coloring matters, colorants, perfumes, surfactants, humectants, preservatives, antiseptics, bactericides, antioxidants, oil agents, viscosity modifier and ultraviolet absorbers can be contained in the cosmetic of the present invention, in addition to the amphoteric urethane resin and silicone polymer.

The cosmetics of the present invention can be prepared, for example, by the following methods.

Preparation of Hair Cosmetics (Foam Hair Fixatives)

In the aqueous solution of the amphoteric urethane resin thus obtained described above, a silicone polymer, various surfactants such as polyoxyethylena alkyl ether, and coconut oil fatty acid diethanolamide, ethanol, deionized water, etc. are blended in the predetermined proportion, and mixed until they are made homogenous to obtain a component X. Then, a component Y made of a propellant (LPG) is added to prepare a desired foam hair fixative.

Preparation of Hair Cosmetics (Aerosol Spray Hair Fixatives)

In the aqueous solution of the above amphoteric urethane resin, a silicone polymer, deionized water, sodium dioctyl sulfosuccinate, ethanol, etc. are blended in the predetermined proportion, and mixed until they are made homogenous to obtain a component X. Then, a component Y made of a propellant (LPG) is added to prepare a desired aerosol spray hair fixative.

Preparation of Hair Cosmetics (Gel-like Hair Fixatives)

First, a viscosity modifier, triethanolamine, ethanol, deionized water, etc. are blended in the predetermined proportion, and then mixed until a viscous gel is formed to obtain a component X. Then, a silicone polymer, ethanol, deionized water, etc. are blended in the aqueous solution of the amphoteric urethane resin in the predetermined proportion to obtain a component Y. The resulting component Y is added to the above component, and mixed until they are made homogenous to prepare a desired gel-like hair fixative.

Preparation of Hair Cosmetics (Pump Spray Hair Fixatives

In the aqueous solution of the amphoteric urethane resin, a silicone polymer, sodium dioctyl sulfosuccinate, ethanol, deionized water, etc. are blended in the predetermined proportion, and mixed until they are made homogenous to prepare a desired pump spray hair fixative.

Furthermore, skin care cosmetics such as shaving cream, skin care lotion and sunscreen lotion; and make-up cosmetics such as nail polish, mascara and foundation can be prepared according to the general preparation methods of these cosmetics.

EXAMPLES

The following Examples and Comparative Examples further illustrate the present invention in detail.

The following materials were prepared before describing the Examples and Comparative Examples.

Amphoteric Urethane Resin (a)

In a glass four-necked flask equipped with a stirrer, a thermometer, a nitrogen introducing tube and a reflux condenser, 100 g of isophorone diisocyanate (IPDI), 60 g of polypropylene glycol (PPG having a molecular weight of 1000), 5 g of cyclohexyl dimethanol (CHDM), and 38 g of dimethylolbutanoic acid (DMBA) were charged, and then 60 g of ethyl acetate as a solvent was added and the mixture was heated to 80 degree C. in an oil bath and allowed to react for four hours. Then, 2 g of N-methyldiethanolamine and 30 g of ethyl acetate were added furthermore, and the mixture was allowed to react for additional three hours. To the resulting mixture, 30 g of polypropylene glycol having an amino group at one end (Jeffamine M1000, manufactured by HUNTSMAN CORPORATION) and 50 g of ethyl acetate were added furthermore, and the mixture was allowed to react for additional one hour to obtain a solution of a polyurethane prepolymer having residual NCO groups. The polyurethane prepolymer having residual NCO groups was dispersed in 750 g of water containing 16 g of potassium hydroxide and then polymerized by the chain-extending reaction at 50 degree C. for three hours. Ethyl acetate was recovered from the resulting water dispersion under reduced pressure to obtain an amphoteric urethane resin which did not substantially contain the solvent.

Amphoteric Urethane Resin (b)

In a glass four-necked flask equipped with a stirrer, a thermometer, a nitrogen introducing tube and a reflux condenser, 100 g of isophorone diisocyanate (IPDI), 60 g of polypropylene glycol (PPG having a molecular weight of 1000), 5 g of cyclohexyl dimethanol (CHDM), 20 g of polyoxyethylene glycol (PEG having a molecular weight of 1000) and, 36 g of dimethylolbutanoic acid (DMBA) were charged, and then 60 g of ethyl acetate as a solvent was added, and the mixture was heated to 80 degree C. in an oil bath and allowed to react for four hours. Then, 2 g of N-methyidiethanolamine and 30 g of ethyl acetate were added furthermore, and the mixture was allowed to react for additional three hours. To the resulting mixture, 30 g of polypropylene glycol having an amino group at one end (Jeffamine M1000, manufactured by HUNTSMAN CORPORATION), and 50 g of ethyl acetate were added furthermore, and the mixture was allowed to react for additional one hour to obtain a solution of a polyurethane prepolymer having residual NCO groups. The polyurethane prepolymer having residual NCO groups was dispersed in 750 g of water containing 15 g of potassium hydroxide and then polymerized by the chain-extending reaction at 50 degree C. for three hours. Ethyl acetate was recovered from the resulting water dispersion under reduced pressure to obtain an aqueous substance of an amphoteric urethane resin which did not substantially contain the solvent and had ethylene oxide chain(s) in the structure.

Amphoteric Urethane Resin (c)

In a glass four-necked flask equipped with a stirrer, a thermometer, a nitrogen introducing tube and a reflux condenser, 100 g of isophorone diisocyanate (IPDI), and 3 g of polydimethylsiloxanediol having two OH groups at one end (molecular weight: 1000) were charged, and then the mixture was heated to 30 degree C. in an oil bath and allowed to react for two hours. Then, 55 g of polypropylene glycol (PPG having a molecular weight of 1000), 10 g of hydrogenated bisphenol A, and 36 g of dimethylolbutanoic acid (DMBA) were added, and then 60 g of ethyl acetate as a solvent was added, and the mixture was heated to 80 degree C. in an oil bath and allowed to react for four hours. Then, 2 g of N-methyldiethano amine and 30 g of ethyl acetate were added furthermore, and the mixture was allowed to react for additional three hours. To the resulting mixture, 30 g of polypropylene glycol having an amino group at one end (Jeffamine M1000, manufactured by HUNTSMAN CORPORATION) and 50 g of ethyl acetate were added furthermore, and the mixture was allowed to react for additional one hour to obtain a solution of a polyurethane prepolymer having residual NCO groups. The polyurethane prepolymer having residual NCO groups was dispersed in 750 g of water containing 15 g of potassium hydroxide and then polymerized by the chain-extending reaction at 50 degree C. for three hours. Ethyl acetate was recovered from the resulting water dispersion under reduced pressure to obtain an aqueous substance of an amphoteric urethane resin which did not substantially contain the solvent and had dimethylsiloxane chain(s) in the structure.

Silicone Polymer (1) (Nonionic)
Methylpolysiloxane (SH200C-2 manufactured by DOW CORNING TORAY SILICONE CO., LTD.)

Silicone Polymer (2) (Polyether-modified)
SH3771C manufactured by DOW CORNING TORAY SILICONE CO., LTD.

Silicone Polymer (3) (Phenyl-modified)
Methylphenylpolysiloxane (SH556 manufactured by DOW CORNING TORAY SILICONE CO., LTD.)

Silicone Polymer (4) (Amino-modified)
Amodimethycone (SM8702C manufactured by DOW CORNING TORAY SILICONE CO., LTD.)

Silicone Polymer (5) (Alkyl-modified)
KF-412 manufactured by SHIN-ETSU CHEMICAL CO., LTD.

Silicone Polymer (6) (Alkoxy-modified)
KF-851 manufactured by SHIN-ETSU CHEMICAL CO., LTD.

Silicone Polymer (7) (Cyclic)
SH245 manufactured by DOW CORNING TORAY SILICONE CO., LTD.

Polyoxyethylene Stearyl Ether
NIKKOL BS-20 manufactured by NIKKO CHEMICALS CO., LTD.

Coconut Oil Fatty Acid Diethanolamide
Amicol CDE-1 manufactured by MIYOSHI OIL & FAT CO., LTD.

Sodium Dioctyl Sulfosuccinate
Monawet MO-70E manufactured by MONA INDUSTRIES INC.

Viscosity Modifier
Alkyl acrylate-polyoxyethylene stearyl ether itaconate copolymer (Structure 2001 manufactured by National Starch and Chemical Company]

Hair Cosmetics (Foam Hair Fixatives)

Examples 1a to 21a, Comparative Examples 1a to 3a

The respective materials of a component X shown in Tables 1 to 4 described hereinafter were blended in the proportion shown in the same tables and mixed until they were made homogenous to obtain the component X. Then, a component Y was added in the resulting component X in the proportion shown in the same tables to prepare a foam hair fixative, respectively. The proportion of the amphoteric urethane resin is represented by a dry weight (the same rule applies correspondingly to the following Examples and Comparative Examples).

Using the foam hair fixatives of the Examples and Comparative Examples thus obtained, the respective characteristics were evaluated according to the following criteria. The results are summarized in Tables 1 to 4 described hereinafter.

Feel
0.8 g of the foam hair fixative was applied to a strand of black virgin hairs (having a length of 25 cm and a weight of 5.0 g). Then, the strand of hairs after drying at room temperature was subjected to an organoleptic test using ten panelists and the feel for hair cosmetic was evaluated. Evaluation criteria are set as follows:

The number of persons, who felt that the strand of hairs is very soft to the feel, is 9 or more.

The number of persons, who felt that the strand of hairs is very soft to the feel, is within a range from 6 to 8.

The number of persons, who felt that the strand of hairs is very soft to the feel, is within a range from 2 to 5.

x: The number of persons, who felt that the strand of hairs is very soft to the feel, is 1 or less.

Spread 0.8 g of the foam hair fixative was applied to a strand of black virgin hairs (having a length of 25 cm and a weight of 5.0 g). Then, the strand was subjected to an organoleptic test using ten panelists and the spread for hair cosmetic was evaluated. Evaluation criteria are set as follows:

The number of persons, who felt that the spread at the time of application is very good, is 9 or more.

The number of persons, who felt that the spread at the time of application is very good, is within a range from 6 to 8.

The number of persons, who felt that the spread at the time of application is very good, is within a range from 2 to 5.

x: The number of persons, who felt that the spread at the time of application is very good, is 1 or less.

Touch 0.8 g of the foam hair fixative was applied on a strand of black virgin hairs (having a length of 25 cm and a weight of 5.0 g). Then, the strand of hairs after drying at room temperature was subjected to an organoleptic test using ten panelists and the touch for hair cosmetic was evaluated. Evaluation criteria are set as follows:

The number of persons, who felt that the strand of hairs after drying is very smooth to the touch, is 9 or more.

The number of persons, who felt that the strand of hairs after drying is very smooth to the touch, is within a range from 6 to 8.

The number of persons, who felt that the strand of hairs after drying is very smooth to the touch, is within a range from 2 to 5.

x: The number of persons, who felt that the strand of hairs after drying is very smooth to the touch, is 1 or less.

Hair Washability 0.6 g of the foam hair fixative was applied to black virgin hairs (having a length of 15 cm and a weight of 3 g), followed by drying to make a strand of hairs. After the strand of hairs was slightly loosen using hot water at 40 degree C., 0.4 9 of a 10% shampoo solution was applied and the strand was washed for 30 seconds. After the strand was rinsed with hot water at 40 degree C. to wash away the shampoo solution, and sufficiently dried at 50 degree C., the hair washability for hair cosmetic were evaluated. Evaluation criteria are set as follows:

The number of persons, who felt that the hair washability are very good because the strand after drying has not any setting ability, is 9 or more.

The number of persons, who felt that the hair washability are very good because the strand after drying has not any setting ability, is within a range from 6 to 8.

The number of persons, who felt that the hair washability are very good because the strand after drying has not any setting ability, is within a range from 2 to 5.

x: The number of persons, who felt that the hair washability are very good because the strand after drying has not any setting ability, is 1 or less.

TABLE 1

(Foam hair Fixative)

(Part) Examples

| | 1a | 2a | 3a | 4a | 5a | 6a | 7a |
|---|---|---|---|---|---|---|---|
| Component X | | | | | | | |
| Amphoteric urethane resin | 3.0 | 3.0 | 3.0 | 3.0 | 3.0 | 3.0 | 3.0 |
| (Types) | (a) | (a) | (a) | (a) | (a) | (a) | (a) |
| Silicone polymer | 0.5 | 0.5 | 0.5 | 0.5 | 0.5 | 0.5 | 0.5 |
| (Types) | (1) | (2) | (3) | (4) | (5) | (6) | (7) |
| Deionized water | 77.2 | 77.2 | 77.2 | 77.2 | 77.2 | 77.2 | 77.2 |
| Polyoxyethylene stearyl ether | 0.5 | 0.5 | 0.5 | 0.5 | 0.5 | 0.5 | 0.5 |
| Ethanol | 10.0 | 10.0 | 10.0 | 10.0 | 10.0 | 10.0 | 10.0 |
| Coconut oil fatty acid diethanolamide | 0.8 | 0.8 | 0.8 | 0.8 | 0.8 | 0.8 | 0.8 |
| Component Y | 8.0 | 8.0 | 8.0 | 8.0 | 8.0 | 8.0 | 8.0 |
| Propellant (LPG) | | | | | | | |
| Feel | | | | | | | |
| Spread | | | | | | | |
| Touch | | | | | | | |
| Hair washability | | | | | | | |

TABLE 2

(Foam Hair Fixative)

(Part) Examples

| | 8a | 9a | 10a | 11a | 12a | 13a | 14a |
|---|---|---|---|---|---|---|---|
| Component X | | | | | | | |
| Amphoteric urethane resin | 3.0 | 3.0 | 3.0 | 3.0 | 3.0 | 3.0 | 3.0 |
| (Types) | (b) | (b) | (b) | (b) | (b) | (b) | (b) |
| Silicone polymer | 0.5 | 0.5 | 0.5 | 0.5 | 0.5 | 0.5 | 0.5 |
| (Types) | (1) | (2) | (3) | (4) | (5) | (6) | (7) |
| Deionized water | 77.2 | 77.2 | 77.2 | 77.2 | 77.2 | 77.2 | 77.2 |
| Polyoxyethylene stearyl ether | 0.5 | 0.5 | 0.5 | 0.5 | 0.5 | 0.5 | 0.5 |
| Ethanol | 10.0 | 10.0 | 10.0 | 10.0 | 10.0 | 10.0 | 10.0 |
| Coconut oil fatty acid diethanolamide | 0.8 | 0.8 | 0.8 | 0.8 | 0.8 | 0.8 | 0.8 |
| Component Y | 8.0 | 8.0 | 8.0 | 8.0 | 8.0 | 8.0 | 8.0 |
| Propellant (LPG) | | | | | | | |
| Feel | | | | | | | |
| Spread | | | | | | | |
| Touch | | | | | | | |
| Hair washability | | | | | | | |

TABLE 3

(Foam Hair Fixative)

(Part) Examples

| | 15a | 16a | 17a | 18a | 19a | 20a | 21a |
|---|---|---|---|---|---|---|---|
| Component X | | | | | | | |
| Amphoteric urethane resin | 3.0 | 3.0 | 3.0 | 3.0 | 3.0 | 3.0 | 3.0 |
| (Types) | (c) | (c) | (c) | (c) | (c) | (c) | (c) |
| Silicone polymer | 0.5 | 0.5 | 0.5 | 0.5 | 0.5 | 0.5 | 0.5 |
| (Types) | (1) | (2) | (3) | (4) | (5) | (6) | (7) |
| Deionized water | 77.2 | 77.2 | 77.2 | 77.2 | 77.2 | 77.2 | 77.2 |

TABLE 3-continued (Foam Hair Fixative)

| | (Part) Examples | | | | | | |
|---|---|---|---|---|---|---|---|
| | 15a | 16a | 17a | 18a | 19a | 20a | 21a |
| Polyoxyethylene stearyl ether | 0.5 | 0.5 | 0.5 | 0.5 | 0.5 | 0.5 | 0.5 |
| Ethanol | 10.0 | 10.0 | 10.0 | 10.0 | 10.0 | 10.0 | 10.0 |
| Coconut oil fatty acid diethanolamide | 0.8 | 0.8 | 0.8 | 0.8 | 0.8 | 0.8 | 0.8 |
| Component Y Propellant (LPG) | 8.0 | 8.0 | 8.0 | 8.0 | 8.0 | 8.0 | 8.0 |
| Feel | | | | | | | |
| Spread | | | | | | | |
| Touch | | | | | | | |
| Hair washability | | | | | | | |

TABLE 4

(Foam Hair Fixative) (Product)

| | Comparative Examples | | |
|---|---|---|---|
| | 1a | 2a | 3a |
| Component X | | | |
| Amphoteric urethane resin | 3.0 | 3.0 | 3.0 |
| (Types) | (a) | (b) | (c) |
| Silicone polymer | — | — | — |
| (Types) | — | — | — |
| Deionized water | 77.7 | 77.7 | 77.7 |
| Polyoxyethylene stearyl ether | 0.5 | 0.5 | 0.5 |
| Ethanol | 10.0 | 10.0 | 10.0 |
| Coconut oil fatty acid diethanolamide | 0.8 | 0.8 | 0.8 |
| Component Y  Propellant (LPG) | 8.0 | 8.0 | 8.0 |
| Feel | | | |
| Spread | | | |
| Touch | | | |
| Hair washability | | | |

As is apparent from the results shown in Tables 1 to 4, the foam hair fixatives of the Examples have very good feel and good spread at the time of application and are superior in touch and hair washability because the amphoteric urethane resin and silicone polymer are used in combination. It is also apparent that the foam hair fixatives of the Examples using the amphoteric urethane resin (b) having ethylene oxide chain(s) in its structure are markedly superior in hair washability. It is also apparent that the foam hair fixatives of the Examples using the amphoteric urethane resin (c) having polysiloxane bonds in its structure are markedly superior in touch.

To the contrary, the foam hair fixatives of the Comparative Examples have good feel because the amphoteric urethane resin is used, but are inferior in spread at the time of application.

Hair Cosmetics (Aerosol Spray Hair Fixatives)

Examples 1b to 21b, Comparative Examples 1b to 3b

The respective materials of a component X shown in Tables 5 to 8 described hereinafter were blended in the proportion shown in the same tables and mixed until they are made homogenous to obtain the component X. Then, a component Y was added in the resulting component X in the proportion shown in the same tables to prepare an aerosol spray hair fixative, respectively.

Using the aerosol spray hair fixatives of the Examples and Comparative Examples thus obtained, the respective characteristics were evaluated according to the criteria for hair cosmetics. The results are summarized in Tables 5 to 8 described hereinafter.

TABLE 5

(Aerosol spray hair fixative)

| | (Parts) Examples | | | | | | |
|---|---|---|---|---|---|---|---|
| | 1b | 2b | 3b | 4b | 5b | 6b | 7b |
| Component X | | | | | | | |
| Amphoteric urethane resin | 3.0 | 3.0 | 3.0 | 3.0 | 3.0 | 3.0 | 3.0 |
| (Types) | (a) | (a) | (a) | (a) | (a) | (a) | (a) |
| Silicone polymer | 0.5 | 0.5 | 0.5 | 0.5 | 0.5 | 0.5 | 0.5 |
| (Types) | (1) | (2) | (3) | (4) | (5) | (6) | (7) |
| Deionized water | 7.0 | 7.0 | 7.0 | 7.0 | 7.0 | 7.0 | 7.0 |
| Sodium dioctyl sulfosuccinate | 0.3 | 0.3 | 0.3 | 0.3 | 0.3 | 0.3 | 0.3 |
| Ethanol | 49.2 | 49.2 | 49.2 | 49.2 | 49.2 | 49.2 | 49.2 |
| Component Y Propellant (LPG) | 40.0 | 40.0 | 40.0 | 40.0 | 40.0 | 40.0 | 40.0 |
| Feel | | | | | | | |
| Spread | | | | | | | |
| Touch | | | | | | | |
| Hair washability | | | | | | | |

TABLE 6

(Aerosol spray hair fixative)

| | (Parts) Examples | | | | | | |
|---|---|---|---|---|---|---|---|
| | 8b | 9b | 10b | 11b | 12b | 13b | 14b |
| Component X | | | | | | | |
| Amphoteric urethane resin | 3.0 | 3.0 | 3.0 | 3.0 | 3.0 | 3.0 | 3.0 |
| (Types) | (b) | (b) | (b) | (b) | (b) | (b) | (b) |
| Silicone polymer | 0.5 | 0.5 | 0.5 | 0.5 | 0.5 | 0.5 | 0.5 |
| (Types) | (1) | (2) | (3) | (4) | (5) | (6) | (7) |
| Deionized water | 7.0 | 7.0 | 7.0 | 7.0 | 7.0 | 7.0 | 7.0 |
| Sodium dioctyl sulfosuccinate | 0.3 | 0.3 | 0.3 | 0.3 | 0.3 | 0.3 | 0.3 |
| Ethanol | 49.2 | 49.2 | 49.2 | 49.2 | 49.2 | 49.2 | 49.2 |
| Component Y Propellant (LPG) | 40.0 | 40.0 | 40.0 | 40.0 | 40.0 | 40.0 | 40.0 |
| Feel | | | | | | | |
| Spread | | | | | | | |
| Touch | | | | | | | |
| Hair washability | | | | | | | |

TABLE 7

(Aerosol spray hair fixative)

| | (Parts) Examples | | | | | | |
|---|---|---|---|---|---|---|---|
| | 15b | 16b | 17b | 18b | 19b | 20b | 21b |
| Component X | | | | | | | |
| Amphoteric urethane resin | 3.0 | 3.0 | 3.0 | 3.0 | 3.0 | 3.0 | 3.0 |
| (Types) | (c) | (c) | (c) | (c) | (c) | (c) | (c) |
| Silicone polymer | 0.5 | 0.5 | 0.5 | 0.5 | 0.5 | 0.5 | 0.5 |
| (Types) | (1) | (2) | (3) | (4) | (5) | (6) | (7) |

TABLE 7-continued (Aerosol spray hair fixative)

| | (Parts) Examples | | | | | | |
|---|---|---|---|---|---|---|---|
| | 15b | 16b | 17b | 18b | 19b | 20b | 21b |
| Deionized water | 7.0 | 7.0 | 7.0 | 7.0 | 7.0 | 7.0 | 7.0 |
| Sodium dioctyl sulfosuccinate | 0.3 | 0.3 | 0.3 | 0.3 | 0.3 | 0.3 | 0.3 |
| Ethanol | 49.2 | 49.2 | 49.2 | 49.2 | 49.2 | 49.2 | 49.2 |
| Component Y Propellant (LPG) | 40.0 | 40.0 | 40.0 | 40.0 | 40.0 | 40.0 | 40.0 |
| Feel | | | | | | | |
| Spread | | | | | | | |
| Touch | | | | | | | |
| Hair washability | | | | | | | |

TABLE 8

(Aerosol spray hair fixative) (Parts)

| | Comparative Examples | | |
|---|---|---|---|
| | 1b | 2b | 3b |
| Component X | | | |
| Amphoteric urethane resin | 3.0 | 3.0 | 3.0 |
| (Types) | (a) | (b) | (c) |
| Silicone polymer | — | — | — |
| (Types) | — | — | — |
| Deionized water | 7.0 | 7.0 | 7.0 |
| Sodium dioctyl sulfosuccinate | 0.3 | 0.3 | 0.3 |
| Ethanol | 49.7 | 49.7 | 49.7 |
| Component Y  Propellant (LPG) | 40.0 | 40.0 | 40.0 |
| Feel | | | |
| Spread | | | |
| Touch | | | |
| Hair washability | | | |

As is apparent from the results shown in Tables 5 to 8, the aerosol spray hair fixatives of the Examples have very good feel and good spread at the time of application and are superior in touch and hair washability because the amphoteric urethane resin and silicone polymer are used in combination. It is also apparent that the aerosol spray hair fixatives of the Examples using the amphoteric urethane resin (b) having ethylene oxide chain(s) in its structure are markedly superior in hair washability. It is also apparent that the aerosol spray hair fixatives of the Examples using the amphoteric urethane resin (c) having polysiloxane bond(s) in its structure are markedly superior in touch.

To the contrary, the aerosol spray hair fixatives of the Comparative Examples have good feel because the amphoteric urethane resin is used, but are inferior in spread at the time of application.

Hair Cosmetics (Ierry Hair Fixatives)

Examples 1c to 2c, Comparative Examples 1c to 3c

The respective materials of a component X shown in Tables 9 to 12 described hereinafter were blended in the proportion shown in the same tables and mixed until viscous gel is formed to obtain the component X. Then, a component Y which was prepared by blending the respective materials in the proportion shown in the same table was added in the resulting component X and mixed until they are made homogenous to prepare a jelly hair fixative, respectively.

Using the jerry hair fixatives of the Examples and Comparative Examples thus obtained, the respective characteristics were evaluated according to the criteria for hair cosmetics. The results are summarized in Tables 9 to 12 described hereinafter.

TABLE 9

(Gel-like hair fixative)

| | (Parts) Examples | | | | | | |
|---|---|---|---|---|---|---|---|
| | 1c | 2c | 3c | 4c | 5c | 6c | 7c |
| Component X | | | | | | | |
| Thickener | 1.5 | 1.5 | 1.5 | 1.5 | 1.5 | 1.5 | 1.5 |
| Triethanolamine | 1.1 | 1.1 | 1.1 | 1.1 | 1.1 | 1.1 | 1.1 |
| Ethanol | 5.0 | 5.0 | 5.0 | 5.0 | 5.0 | 5.0 | 5.0 |
| Deionized water | 50.0 | 50.0 | 50.0 | 50.0 | 50.0 | 50.0 | 50.0 |
| Component Y | | | | | | | |
| Amphoteric urethane resin | 3.0 | 3.0 | 3.0 | 3.0 | 3.0 | 3.0 | 3.0 |
| (Types) | (a) | (a) | (a) | (a) | (a) | (a) | (a) |
| Silicone polymer | 0.5 | 0.5 | 0.5 | 0.5 | 0.5 | 0.5 | 0.5 |
| (Types) | (1) | (2) | (3) | (4) | (5) | (6) | (7) |
| Ethanol | 5.0 | 5.0 | 5.0 | 5.0 | 5.0 | 5.0 | 5.0 |
| Deionized water | 33.9 | 33.9 | 33.9 | 33.9 | 33.9 | 33.9 | 33.9 |
| Feel | | | | | | | |
| Spread | | | | | | | |
| Touch | | | | | | | |
| Hair washability | | | | | | | |

TABLE 10

(Gel-like hair fixative)

| | (Parts) Examples | | | | | | |
|---|---|---|---|---|---|---|---|
| | 8c | 9c | 10c | 11c | 12c | 13c | 14c |
| Component X | | | | | | | |
| Thickener | 1.5 | 1.5 | 1.5 | 1.5 | 1.5 | 1.5 | 1.5 |
| Triethanolamine | 1.1 | 1.1 | 1.1 | 1.1 | 1.1 | 1.1 | 1.1 |
| Ethanol | 5.0 | 5.0 | 5.0 | 5.0 | 5.0 | 5.0 | 5.0 |
| Deionized water | 50.0 | 50.0 | 50.0 | 50.0 | 50.0 | 50.0 | 50.0 |
| Component Y | | | | | | | |
| Amphoteric urethane resin | 3.0 | 3.0 | 3.0 | 3.0 | 3.0 | 3.0 | 3.0 |
| (Types) | (b) | (b) | (b) | (b) | (b) | (b) | (b) |
| Silicone polymer | 0.5 | 0.5 | 0.5 | 0.5 | 0.5 | 0.5 | 0.5 |
| (Types) | (1) | (2) | (3) | (4) | (5) | (6) | (7) |
| Ethanol | 5.0 | 5.0 | 5.0 | 5.0 | 5.0 | 5.0 | 5.0 |
| Deionized water | 33.9 | 33.9 | 33.9 | 33.9 | 33.9 | 33.9 | 33.9 |
| Feel | | | | | | | |
| Spread | | | | | | | |
| Touch | | | | | | | |
| Hair washability | | | | | | | |

TABLE 11

(Gel-like hair fixative)

| | (Parts) Examples | | | | | | |
|---|---|---|---|---|---|---|---|
| | 15c | 16c | 17c | 18c | 19c | 20c | 21c |
| Component X | | | | | | | |
| Thickener | 1.5 | 1.5 | 1.5 | 1.5 | 1.5 | 1.5 | 1.5 |
| Triethanolamine | 1.1 | 1.1 | 1.1 | 1.1 | 1.1 | 1.1 | 1.1 |
| Ethanol | 5.0 | 5.0 | 5.0 | 5.0 | 5.0 | 5.0 | 5.0 |

TABLE 11-continued (Gel-like hair fixative)

(Parts) Examples

| | 15c | 16c | 17c | 18c | 19c | 20c | 21c |
|---|---|---|---|---|---|---|---|
| Deionized water | 50.0 | 50.0 | 50.0 | 50.0 | 50.0 | 50.0 | 50.0 |
| Component Y | | | | | | | |
| Amphoteric urethane resin | 3.0 | 3.0 | 3.0 | 3.0 | 3.0 | 3.0 | 3.0 |
| (Types) | (c) | (c) | (c) | (c) | (c) | (c) | (c) |
| Silicone polymer | 0.5 | 0.5 | 0.5 | 0.5 | 0.5 | 0.5 | 0.5 |
| (Types) | (1) | (2) | (3) | (4) | (5) | (6) | (7) |
| Ethanol | 5.0 | 5.0 | 5.0 | 5.0 | 5.0 | 5.0 | 5.0 |
| Deionized water | 33.9 | 33.9 | 33.9 | 33.9 | 33.9 | 33.9 | 33.9 |
| Feel | | | | | | | |
| Spread | | | | | | | |
| Touch | | | | | | | |
| Hair washability | | | | | | | |

TABLE 12

(Gel-like hair fixative) (Parts)

Comparative Examples

| | 1c | 2c | 3c |
|---|---|---|---|
| Component X | | | |
| Thickener | 1.5 | 1.5 | 1.5 |
| Triethanolamine | 1.1 | 1.1 | 1.1 |
| Ethanol | 5.0 | 5.0 | 5.0 |
| Deionized water | 50.0 | 50.0 | 50.0 |
| Component Y | | | |
| Amphoteric urethane resin | 3.0 | 3.0 | 3.0 |
| (Types) | (a) | (b) | (c) |
| Silicone polymer | — | — | — |
| (Types) | — | — | — |
| Ethanol | 5.0 | 5.0 | 5.0 |
| Deionized water | 34.4 | 34.4 | 34.4 |
| Feel | | | |
| Spread | | | |
| Touch | | | |
| Hair washability | | | |

As is apparent from the results shown in Tables 9 to 12, the jelly hair fixatives of the Examples have very good feel and good spread at the time of application and are superior in touch and hair washability because the amphoteric urethane resin and silicone polymer are used in combination. It is also apparent that the gel-like hair fixatives of the Examples using the amphoteric urethane resin (b) having ethylene oxide chain(s) in its structure are markedly superior in hair washability. It is also apparent that the gel-like hair fixatives of the Examples using the amphoteric urethane resin (c) having polysiloxane bond(s) in its structure are markedly superior in touch.

To the contrary, the gel-like hair fixatives of the Comparative Examples have good feel because the amphoteric urethane resin is used, but are inferior in spread at the time of application.

Hair Cosmetics (Pump Spray Hair Fixatives)

Examples 1d to 21d, Comparative Examples 1d to 3d

The respective materials shown in Tables 13 to 16 described hereinafter were blended in the proportion shown in the same table and mixed until they are made homogenous to prepare a pump spray hair fixative, respectively.

Using the pump spray hair fixatives of the Examples and Comparative Examples thus obtained, the respective characteristics were evaluated according to the criteria for hair cosmetics. The results are summarized in Tables 13 to 16 described hereinafter.

TABLE 13

(Pump spray hair fixative)

(Parts) Examples

| | 1d | 2d | 3d | 4d | 5d | 6d | 7d |
|---|---|---|---|---|---|---|---|
| Amphoteric urethane resin | 3.0 | 3.0 | 3.0 | 3.0 | 3.0 | 3.0 | 3.0 |
| (Types) | (a) | (a) | (a) | (a) | (a) | (a) | (a) |
| Silicone polymer | 0.5 | 0.5 | 0.5 | 0.5 | 0.5 | 0.5 | 0.5 |
| (Types) | (1) | (2) | (3) | (4) | (5) | (6) | (7) |
| Sodium dioctyl sulfosuccinate | 0.3 | 0.3 | 0.3 | 0.3 | 0.3 | 0.3 | 0.3 |
| Ethanol | 10.0 | 10.0 | 10.0 | 10.0 | 10.0 | 10.0 | 10.0 |
| Deionized water | 86.2 | 86.2 | 86.2 | 86.2 | 86.2 | 86.2 | 86.2 |
| Feel | | | | | | | |
| Spread | | | | | | | |
| Touch | | | | | | | |
| Hair washability | | | | | | | |

TABLE 14

(Pump spray hair fixative)

(Parts) Examples

| | 8d | 9d | 10d | 11d | 12d | 13d | 14d |
|---|---|---|---|---|---|---|---|
| Amphoteric urethane resin | 3.0 | 3.0 | 3.0 | 3.0 | 3.0 | 3.0 | 3.0 |
| (Types) | (b) | (b) | (b) | (b) | (b) | (b) | (b) |
| Silicone polymer | 0.5 | 0.5 | 0.5 | 0.5 | 0.5 | 0.5 | 0.5 |
| (Types) | (1) | (2) | (3) | (4) | (5) | (6) | (7) |
| Sodium dioctyl sulfosuccinate | 0.3 | 0.3 | 0.3 | 0.3 | 0.3 | 0.3 | 0.3 |
| Ethanol | 10.0 | 10.0 | 10.0 | 10.0 | 10.0 | 10.0 | 10.0 |
| Deionized water | 86.2 | 86.2 | 86.2 | 86.2 | 86.2 | 86.2 | 86.2 |
| Feel | | | | | | | |
| Spread | | | | | | | |
| Touch | | | | | | | |
| Hair washability | | | | | | | |

TABLE 15

(Pump spray hair fixative)

(Parts) Examples

| | 15d | 16d | 17d | 18d | 19d | 20d | 21d |
|---|---|---|---|---|---|---|---|
| Amphoteric urethane resin | 3.0 | 3.0 | 3.0 | 3.0 | 3.0 | 3.0 | 3.0 |
| (Types) | (c) | (c) | (c) | (c) | (c) | (c) | (c) |
| Silicone polymer | 0.5 | 0.5 | 0.5 | 0.5 | 0.5 | 0.5 | 0.5 |
| (Types) | (1) | (2) | (3) | (4) | (5) | (6) | (7) |
| Sodium dioctyl sulfosuccinate | 0.3 | 0.3 | 0.3 | 0.3 | 0.3 | 0.3 | 0.3 |
| Ethanol | 10.0 | 10.0 | 10.0 | 10.0 | 10.0 | 10.0 | 10.0 |
| Deionized water | 86.2 | 86.2 | 86.2 | 86.2 | 86.2 | 86.2 | 86.2 |
| Feel | | | | | | | |
| Spread | | | | | | | |
| Touch | | | | | | | |
| Hair washability | | | | | | | |

TABLE 16

(Pump spray hair fixative) (Parts)

| | Comparative Examples | | |
|---|---|---|---|
| | 1d | 2d | 3d |
| Amphoteric urethane resin | 3.0 | 3.0 | 3.0 |
| (Types) | (a) | (b) | (c) |
| Silicone polymer | — | — | — |
| (Types) | — | — | — |
| Sodium dioctyl sulfosuccinate | 0.3 | 0.3 | 0.3 |
| Ethanol | 10.0 | 10.0 | 10.0 |
| Deionized water | 86.7 | 86.7 | 86.7 |
| Feel | | | |
| Spread | | | |
| Touch | | | |
| Hair washability | | | |

As is apparent from the results shown in Tables 13 to 16, the pump spray hair fixatives of the Examples have very good feel and good spread at the time of application and are superior in touch and hair washability because the amphoteric urethane resin and silicone polymer are used in combination. It is also apparent that the pump spray hair fixatives of the Examples using the amphoteric urethane resin (b) having ethylene oxide chain(s) in its structure are markedly superior in hair washability. It is also apparent that the pump spray hair fixatives of the Examples using the amphoteric urethane resin (c) having polysiloxane bond(s) in its structure are markedly superior in feel.

To the contrary, the pump spray hair fixatives of the Comparative Examples have good feel because the amphoteric urethane resin is used, but are inferior in spread at the time of application.

Skin Care Cosmetics (Skin Care Lotions)

Examples 1e to 7e, Comparative Example 1e

The respective materials of a component X shown in Tables 17 and 18 described hereinafter were blended in the proportion shown in the same tables and heated to 80 degree C. to obtain the component X. The respective materials of a component Y were blended in the proportion shown in the same tables and heated to 80 degree C. to obtain the component Y. Then, the component X and component Y were mixed, followed by stirring at 80 degree C. for 30 minutes. A viscosity modifier was added, and mixed until they were made homogenous, then cooled down to 40 degree C. to prepare a skin care lotion, respectively.

Using the skin care lotions of the Examples and Comparative Example thus obtained, the respective characteristics were evaluated according to the following criteria. The results are summarized in Tables 17 and 18 described hereinafter.

Feel

The feel for skin care cosmetic was evaluated at a practical use test using ten panelists. Evaluation criteria are set as follows:

The number of persons, who did not feel tight and also felt soft, is 9 or more.

The number of persons, who did not feel tight and also felt soft, is within a range from 6 to 8.

The number of persons, who did not feel tight and also felt soft, is within a range from 2 to 5.

x: The number of persons, who did not feel tight and also felt soft, is 1 or less.

Spread

The spread for skin care cosmetic was evaluated by a practical use test using ten panelists. Evaluation criteria are set as follows:

The number of persons, who felt that the spread at the time of application is very good, is 9 or more.

The number of persons, who felt that the spread at the time of application is very good, is within a range from 6 to 8.

The number of persons, who felt that the spread at the time of application is very good, is within a range from 2 to 5.

x: The number of persons, who felt that the spread at the time of application is very good, is 1 or less.

TABLE 17

(Skin care lotion) (Parts)

| | Examples | | | |
|---|---|---|---|---|
| | 1e | 2e | 3e | 4e |
| Component X | | | | |
| Octyl methoxycinnamate | 7.5 | 1.5 | 7.5 | 7.5 |
| Ether polyoxystearate | 1.0 | 1.0 | 1.0 | 1.0 |
| Emulsion type glyceryl stearate | 1.0 | 1.0 | 1.0 | 1.0 |
| Stearic acid | 1.5 | 1.5 | 1.5 | 1.5 |
| Mixture of titanium dioxide and $C_{12-15}$ alkyl benzoate | 1.7 | 1.7 | 1.7 | 1.7 |
| Polyoxyethylene-added dimethycone | 0.5 | 0.5 | 0.5 | 0.5 |
| Component Y | | | | |
| Amphoteric urethane resin (a) | 1.0 | 1.0 | 1.0 | 1.0 |
| Silicone polymer | 0.3 | 0.3 | 0.3 | 0.3 |
| (Types) | (1) | (2) | (3) | (4) |
| Deionized water | 61.5 | 61.5 | 61.5 | 61.5 |
| Triethanolamine (99%) | 4.0 | 4.0 | 4.0 | 4.0 |
| Antiseptic | q.s. | q.s. | q.s. | q.s. |
| Thickener (2%) | 20.0 | 20.0 | 20.0 | 20.0 |
| Feel | | | | |
| Spread | | | | |

TABLE 18

(Skin care lotion) (Parts)

| | Examples | | | Comparative Example |
|---|---|---|---|---|
| | 5e | 6e | 7e | 1e |
| Component X | | | | |
| Octyl methoxycinnamate | 7.5 | 7.5 | 7.5 | 7.5 |
| Ether polyoxystearate | 1.0 | 1.0 | 1.0 | 1.0 |
| Emulsion type glyceryl stearate | 1.0 | 1.0 | 1.0 | 1.0 |
| Stearic acid | 1.5 | 1.5 | 1.5 | 1.5 |
| Mixture of titanium dioxide and $C_{12-15}$ alkyl benzoate | 1.7 | 1.7 | 1.7 | 1.7 |
| Polyoxyethylene-added dimethycone | 0.5 | 0.5 | 0.5 | 0.5 |
| Component Y | | | | |
| Amphoteric urethane resin (a) | 1.0 | 1.0 | 1.0 | 1.0 |
| Silicone polymer | 0.3 | 0.3 | 0.3 | — |
| (Types) | (5) | (6) | (7) | — |
| Deionized water | 61.5 | 61.5 | 61.5 | 61.8 |
| Triethanolamine (99%) | 4.0 | 4.0 | 4.0 | 4.0 |
| Antiseptic | q.s. | q.s. | q.s. | q.s. |
| Thickener (2%) | 20.0 | 20.0 | 20.0 | 20.0 |
| Feel | | | | |
| Spread | | | | |

As is apparent from the results shown in Tables 17 and 18, the skin care lotions of the Examples have very good feel and good spread at the time of application because the amphoteric urethane resin and silicone polymer are used in combination.

To the contrary, the skin care lotion of the Comparative Example has good feel because the amphoteric urethane resin is used, but is inferior in spread at the time of application.

Skin Care Cosmetics (Shaving Creams)

Examples 1f to 7f, Comparative Example 1f

The respective materials of a component X shown in Tables 19 and 20 described hereinafter were blended in the proportion shown in the same tables and heated to 80 degree C. to obtain the component X. The respective materials of a component Y were blended in the proportion shown in the same tables and heated to 80 degree C. to obtain the component Y. Then, the component X and component Y were mixed at 80 degree C. and cooled down to 40 degree C. An antiseptic and a perfume were added in a sufficient quantity to prepare shaving cream, respectively.

Using the shaving creams of the Examples and Comparative Example thus obtained, the respective characteristics were evaluated according to the criteria for skin care cosmetics. The results are summarized in Tables 19 and 20 described hereinafter.

TABLE 19

(Shaving cream) (Parts)

| | Examples | | | |
|---|---|---|---|---|
| | 1f | 2f | 3f | 4f |
| Component X | | | | |
| Stearic acid | 8.0 | 8.0 | 8.0 | 8.0 |
| Mineral oil | 2.0 | 2.0 | 2.0 | 2.0 |
| Isopropyl myristate | 2.0 | 2.0 | 2.0 | 2.0 |
| Glyceryl stearate | 0.5 | 0.5 | 0.5 | 0.5 |
| Component Y | | | | |
| Amphoteric urethane resin (a) | 0.5 | 0.5 | 0.5 | 0.5 |
| Silicone polymer | 0.3 | 0.3 | 0.3 | 0.3 |
| (Types) | (1) | (2) | (3) | (4) |
| Deionized water | 72.5 | 72.5 | 72.5 | 72.5 |
| Thickeners (2%) | 10.0 | 10.0 | 10.0 | 10.0 |
| Triethanolamine (99%) | 4.2 | 4.2 | 4.2 | 4.2 |
| Feel | | | | |
| Spread | | | | |

TABLE 20

(Shaving cream) (Parts)

| | Examples | | | Comparative Example |
|---|---|---|---|---|
| | 5f | 6f | 7f | 1f |
| Component X | | | | |
| Stearic acid | 8.0 | 8.0 | 8.0 | 8.0 |
| Mineral oil | 2.0 | 2.0 | 2.0 | 2.0 |
| Isopropyl myristate | 2.0 | 2.0 | 2.0 | 2.0 |
| Glyceryl stearate | 0.5 | 0.5 | 0.5 | 0.5 |
| Component Y | | | | |
| Amphoteric urethane resin (a) | 0.5 | 0.5 | 0.5 | 0.5 |
| Silicone polymer | 0.3 | 0.3. | 0.3 | — |
| (Types) | (5) | (6) | (7) | — |
| Deionized water | 72.5 | 72.5 | 72.5 | 72.5 |
| Thickeners (2%) | 10.0 | 10.0 | 10.0 | 10.0 |
| Triethanolamine (99%) | 4.2 | 4.2 | 4.2 | 4.2 |
| Feel | | | | |
| Spread | | | | |

As is apparent from the results shown in Tables 19 and 20, the shaving creams of the Examples have very good feel and good spread at the time of application because the amphoteric urethane resin and silicone polymer are used in combination.

To the contrary, the shaving cream of the Comparative Example has good feel because the amphoteric urethane resin is used, but is inferior in spread at the time of application.

Skin Care Cosmetics (Sunscreen Lotions)

Examples 1g to 7g, Comparative Example 1a

The respective materials of a component X shown in Tables 21 and 22 described hereinafter were blended in the proportion shown in the same tables and heated to 80 degree C. to obtain the component X. The respective materials of a component Y were blended in the proportion shown in the same tables and heated to 80 degree C. to obtain the component Y. Then, the component X and component Y were mixed at 80 degree C. to prepare a sunscreen lotion, respectively.

Using the sunscreen lotions of the Examples and Comparative Example thus obtained, the respective characteristics were evaluated according to the criteria for skin care cosmetics. The results are summarized in Tables 21 and 22 described hereinafter.

TABLE 21

(Sunscreen lotion) (Parts)

| | Examples | | | |
|---|---|---|---|---|
| | 1g | 2g | 3g | 4g |
| Component X | | | | |
| Octyl cinnamate | 7.50 | 7.50 | 7.50 | 7.50 |
| Octyl palmitate | 5.00 | 5.00 | 5.00 | 5.00 |
| Cetyl alcohol | 1.00 | 1.00 | 1.00 | 1.00 |
| Polyethylene glycol monostearate | 1.50 | 1.50 | 1.50 | 1.50 |
| Poly(oxyethylene oxypropylene) methyl-polysiloxane copolymer | 1.00 | 1.00 | 1.00 | 1.00 |
| Dimethylstearylamine | 2.00 | 2.00 | 2.00 | 2.00 |
| Component Y | | | | |
| Amphoteric urethane resin (a) | 1.00 | 1.00 | 1.00 | 1.00 |
| Silicone polymer | 0.50 | 0.50 | 0.50 | 0.50 |
| (Types) | (1) | (2) | (3) | (4) |
| Purified water | 69.55 | 69.55 | 69.55 | 69.55 |
| Triethanolamine (99%) | 0.70 | 0.70 | 0.70 | 0.70 |
| Thickeners (2%) | 10.00 | 10.00 | 10.00 | 10.00 |
| Antiseptic | 0.25 | 0.25 | 0.25 | 0.25 |
| Feel | | | | |
| Spread | | | | |

TABLE 22

(Sunscreen lotion) (Parts)

|  | Examples | | | Comparative Example |
|---|---|---|---|---|
|  | 5g | 6g | 7g | 1g |
| Component X |  |  |  |  |
| Octyl cinnamate | 7.50 | 7.50 | 7.50 | 7.50 |
| Octyl palmitate | 5.00 | 5.00 | 5.00 | 5.00 |
| Cetyl alcohol | 1.00 | 1.00 | 1.00 | 1.00 |
| Polyethylene glycol monostearate | 1.50 | 1.50 | 1.50 | 1.50 |
| Poly(oxyethylene oxypropylene) methyl-polysiloxane copolymer | 1.00 | 1.00 | 1.00 | 1.00 |
| Dimethylstearylamine | 2.00 | 2.00 | 2.00 | 2.00 |
| Component Y |  |  |  |  |
| Amphoteric urethane resin (a) | 1.00 | 1.00 | 1.00 | 1.00 |
| Silicone polymer | 0.50 | 0.50 | 0.50 | — |
| (Types) | (5) | (6) | (7) | — |
| Purified water | 69.55 | 69.55 | 69.55 | 70.05 |
| Triethanolamine (99%) | 0.70 | 0.70 | 0.70 | 0.70 |
| Thickeners (2%) | 10.00 | 10.00 | 10.00 | 10.00 |
| Antiseptic | 0.25 | 0.25 | 0.25 | 0.25 |
| Feel |  |  |  |  |
| Spread |  |  |  |  |

As is apparent from the results shown in Tables 21 and 22, the sunscreen lotions of the Examples have very good feel and good spread at the time of application because the amphoteric urethane resin and silicone polymer are used in combination.

To the contrary, the sunscreen lotion of the Comparative Example has good feel because the amphoteric urethane resin is used, but is inferior in spread at the time of application.

Make-up Cosmetics (Nail Polishs)

Examples 1h to 7h, Comparative Example 1h

As shown in Tables 23 and 24 described hereinafter, a pigment was dispersed in deionized water in the proportion shown in the same tables and other components were added in the proportion shown in the same tables. The resultant was mixed until it was made homogenous with stirring and deaerated to prepare a nail polish, respectively.

Using the nail polishs of the Examples and Comparative Example thus obtained, the respective characteristics were evaluated according to the following criteria. The results are summarized in Tables 23 and 24 described hereinafter.

Feel

The feel for skin care cosmetic was evaluated at a practical use test using ten panelists. Evaluation criteria are set as follows:

The number of persons, who did not feel tight and also felt soft, is 9 or more.

The number of persons, who did not feel tight and also felt soft, is within a range from 6 to 8.

The number of persons, who did not feel tight and also felt soft, is within a range from 2 to 5.

x: The number of persons, who did not feel tight and also felt soft, is 1 or less.

Spread

The spread for skin care cosmetic was evaluated at a practical use test using ten panelists. Evaluation criteria are set as follows:

The number of persons, who felt that the spread at the time of application is very good, is 9 or more.

The number of persons, who felt that the spread at the time of application is very good, is within a range from 6 to 8;

The number of persons, who felt that the spread at the time of application is very good, is within a range from 2 to 5.

x: The number of persons, who felt that the spread at the time of application is very good, is 1 or less.

TABLE 23

(Nail Polish) (Parts)

|  | Examples | | | |
|---|---|---|---|---|
|  | 1h | 2h | 3h | 4h |
| Water phase |  |  |  |  |
| Amphoteric urethane resin (a) | 10.0 | 10.0 | 10.0 | 10.0 |
| Silicone polymer | 0.5 | 0.5 | 0.5 | 0.5 |
| (Types) | (1) | (2) | (3) | (4) |
| Deionized water | 86.1 | 86.1 | 86.1 | 88.1 |
| Bentonite | 0.6 | 0.6 | 0.6 | 0.6 |
| Pigment | 2.5 | 2.5 | 2.5 | 2.5 |
| Others |  |  |  |  |
| Perfume | 0.1 | 0.1 | 0.1 | 0.1 |
| Antiseptic | 0.1 | 0.1 | 0.1 | 0.1 |
| Silicone defoamer | 0.1 | 0.1 | 0.1 | 0.1 |
| Feel |  |  |  |  |
| Spread |  |  |  |  |

TABLE 24

(Nail polish) (Parts)

|  | Examples | | | Comparative Example |
|---|---|---|---|---|
|  | 5h | 8h | 7h | 1h |
| Water phase |  |  |  |  |
| Amphoteric urethane resin (a) | 10.0 | 10.0 | 10.0 | 10.0 |
| Silicone polymer | 0.5 | 0.5 | 0.5 | — |
| (Types) | (5) | (6) | (7) | — |
| Deionized water | 88.1 | 86.1 | 86.1 | 86.1 |
| Bentonite | 0.6 | 0.6 | 0.8 | 0.6 |
| Pigment | 2.5 | 2.5 | 2.5 | 2.5 |
| Others |  |  |  |  |
| Perfume | 0.1 | 0.1 | 0.1 | 0.1 |
| Antiseptic | 0.1 | 0.1 | 0.1 | 0.1 |
| Silicone defoamer | 0.1 | 0.1 | 0.1 | 0.1 |
| Feel |  |  |  |  |
| Spread |  |  |  |  |

As is apparent from the results shown in Tables 23 to 24, the nail polishes of the Examples have very good feel and good spread at the time of application because the amphoteric urethane resin and silicone polymer are used in combination.

To the contrary, the nail polish of the Comparative Example has good feel because the amphoteric urethane resin is used, but is inferior in spread at the time of application.

Make-up Cosmetics (Mascaras)

Examples 1to 7i, Comparative Example 1i

As shown in Tables 25 and 26 described hereinafter, propylene glycol, triethanolamine, a viscosity modifier, and an antiseptic were blended with purified water in the proportion shown in the same tables and, after dissolving them at 80 degree C., the pigment was dispersed therein to form a water phase. Then, the respective materials of a component Z were blended in the proportion shown in the same tables and dissolved at 80 degree C. to form an oil phase. The oil phase was aded to the water phase and the mixture was emulsified by using a homogenizing mixer. Then, the respective materials of a component Y were gradually charged in the proportion shown in the same tables, followed by stirring using a homogenizing mixer and further cooled down to room temperature to prepare a mascara, respectively.

Using the mascaras of the Examples and Comparative Example thus obtained, the respective characteristics were evaluated according to the criteria for make-up cosmetics. The results are summarized in Tables 25 and 26 described hereinafter.

TABLE 25

(Mascara) (Parts)

|  | Examples | | | |
|---|---|---|---|---|
|  | 1i | 2i | 3i | 4i |
| Component X | | | | |
| Propylene glycol | 5.0 | 5.0 | 5.0 | 5.0 |
| Triethanolamine | 1.0 | 1.0 | 1.0 | 1.0 |
| Thickener (2%) | 10.0 | 10.0 | 10.0 | 10.0 |
| Antiseptic | 0.5 | 0.5 | 0.5 | 0.5 |
| Pigment | 10.0 | 10.0 | 10.0 | 10.0 |
| Purified water | 51.0 | 51.0 | 51.0 | 51.0 |
| Component Y | | | | |
| Amphoteric urethane resin (a) | 10.0 | 10.0 | 10.0 | 10.0 |
| Silicone polymer | 0.5 | 0.5 | 0.5 | 0.5 |
| (Types) | (1) | (2) | (3) | (4) |
| Component Z | | | | |
| Stearic acid | 6.0 | 6.0 | 6.0 | 6.0 |
| Beeswax | 6.0 | 6.0 | 6.0 | 6.0 |
| Feel | | | | |
| Spread | | | | |

TABLE 26

(Mascara) (Parts)

|  | Examples | | | Comparative Example |
|---|---|---|---|---|
|  | 5i | 6i | 7i | 1i |
| Component X | | | | |
| Propylene glycol | 5.0 | 5.0 | 5.0 | 5.0 |
| Triethanolamine | 1.0 | 1.0 | 1.0 | 1.0 |
| Thickener (2%) | 10.0 | 10.0 | 10.0 | 10.0 |
| Antiseptic | 0.5 | 0.5 | 0.5 | 0.5 |
| Pigment | 10.0 | 10.0 | 10.0 | 10.0 |
| Purified water | 51.0 | 51.0 | 51.0 | 51.0 |
| Component Y | | | | |
| Amphoteric urethane resin (a) | 10.0 | 10.0 | 10.0 | 10.0 |
| Silicone polymer | 0.5 | 0.5 | 0.5 | 0.5 |
| (Types) | (1) | (2) | (3) | (4) |
| Component Z | | | | |
| Stearic acid | 6.0 | 6.0 | 6.0 | 6.0 |
| Beeswax | 6.0 | 6.0 | 6.0 | 6.0 |
| Feel | | | | |
| Spread | | | | |

As is apparent from the results shown in Tables 25 and 26, the mascaras of the Examples have very good feel and good spread at the time of application because the amphoteric urethane resin and silicone polymer are used in combination To the contrary, the mascara of the Comparative Example has good feel because the amphoteric urethane resin is used, but is inferior in spread at the time of application.

Make-up Cosmetics (Foundations)

Examples 1j to 7j, Comparative Examples 1j (i) Preparation of Pigment

The respective components shown in Tables 27 and 28 described hereinafter were mixed in the proportion shown in the same tables and then pulverized through a pulverizer to prepare a pigment.

(ii) Preparation of Water Phase

Deionized water was heated to 70 degree C. and bentonite was added to make swollen. Then, sodium carboxymethylcellulose dispersed previously in propylene glycol was dissolved by adding to the resulting solution. Triethanolamine, methylparaoxybenozate, and one selected from amphoteric urethane resin or a silicone polymer were added and dissolved thereto to prepare a water phase.

(iii) Preparation of Oil Phase

The respective components shown in Tables 27 and 28 described hereinafter were mixed in the proportion shown in the same tables and then dissolved with heating to prepare an oil phase.

(iv) Preparation of Pigment Dispersion

A pigment dispersion was prepared by adding the above pigment to the water phase with stirring, followed by passing through a colloid mill.

(v) Emulsification

The above pigment dispersion and oil phase were heated to 75 degree C. and 80 degree C., respectively, and the above oil phase was added to the pigment dispersion with stirring. After cooling the dispersion, a perfume was added at 45 degree C., and the stirring was continued up to the room temperature to prepare a foundation, respectively.

Using the foundations of the Examples and Comparative Example thus obtained, the respective characteristics were evaluated according to the criteria for make-up cosmetics. The results are summarized in Tables 27 and 28 described hereinafter.

TABLE 27

(Foundation) (Parts)

|  | Examples | | | |
|---|---|---|---|---|
|  | 1j | 2j | 3j | 4j |
| Oil phase | | | | |
| Stearic acid | 2.4 | 2.4 | 2.4 | 2.4 |
| Propylene glycol monostearate | 2.0 | 2.0 | 2.0 | 2.0 |
| Cetostearyl alcohol | 0.2 | 0.2 | 0.2 | 0.2 |
| Liquid lanolin | 2.0 | 2.0 | 2.0 | 2.0 |
| Liquid paraffin | 3.0 | 3.0 | 3.0 | 3.0 |
| Isopropyl myristate | 8.5 | 8.5 | 8.5 | 8.5 |
| Propyl paraoxybenzoate | q.s. | q.s. | q.s. | q.s. |
| Water phase | | | | |
| Amphoteric urethane resin (a) | 0.5 | 0.5 | 0.5 | 0.5 |
| Silicone polymer | 0.3 | 0.3 | 0.3 | 0.3 |
| (Types) | (1) | (2) | (3) | (4) |
| Deionized water | 63.3 | 63.3 | 63.3 | 63.3 |
| Sodium carboxymethylcellulose | 0.2 | 0.2 | 0.2 | 0.2 |
| Bentonite | 0.5 | 0.5 | 0.5 | 0.5 |
| Propylene glycol | 4.0 | 4.0 | 4.0 | 4.0 |
| Triethanolamine | 1.1 | 1.1 | 1.1 | 1.1 |
| Methyl paraoxybenzoate | q.s. | q.s. | q.s. | q.s. |

TABLE 27-continued (Foundation) (Parts)

| | Examples | | | |
|---|---|---|---|---|
| | 1j | 2j | 3j | 4j |
| Pigment | | | | |
| Titanium oxide | 8.0 | 8.0 | 8.0 | 8.0 |
| Talc | 4.0 | 4.0 | 4.0 | 4.0 |
| Coloring pigment | q.s. | q.s. | q.s. | q.s. |
| Perfume | q.s. | q.s. | q.s. | q.s. |
| Feel | | | | |
| Spread | | | | |

TABLE 28

(Foundation) (Parts)

| | Examples | | | Comparative Example |
|---|---|---|---|---|
| | 5j | 6j | 7j | 1j |
| Oil phase | | | | |
| Stearic acid | 2.4 | 2.4 | 2.4 | 2.4 |
| Propylene glycol monostearate | 2.0 | 2.0 | 2.0 | 2.0 |
| Cetostearyl alcohol | 0.2 | 0.2 | 0.2 | 0.2 |
| Liquid lanolin | 2.0 | 2.0 | 2.0 | 2.0 |
| Liquid paraffin | 3.0 | 3.0 | 3.0 | 3.0 |
| Isopropyl myristate | 8.5 | 8.5 | 8.5 | 8.5 |
| Propyl paraoxybenzoate | q.s. | q.s. | q.s. | q.s. |
| Water phase | | | | |
| Amphoteric urethane resin (a) | 0.5 | 0.5 | 0.5 | 0.5 |
| Silicone polymer | 0.3 | 0.3 | 0.3 | — |
| (Types) | (5) | (6) | (7) | — |
| Deionized water | 63.3 | 63.3 | 63.3 | 63.6 |
| Sodium carboxymethylcellulose | 0.2 | 0.2 | 0.2 | 0.2 |
| Bentonite | 0.5 | 0.5 | 0.5 | 0.5 |
| Propylene glycol | 4.0 | 4.0 | 4.0 | 4.0 |
| Triethanolamine | 1.1 | 1.1 | 1.1 | 1.1 |
| Methyl paraoxybenzoate | q.s. | q.s. | q.s. | q.s. |
| Pigment | | | | |
| Titanium oxide | 8.0 | 8.0 | 8.0 | 8.0 |
| Talc | 4.0 | 4.0 | 4.0 | 4.0 |
| Coloring pigment | q.s. | q.s. | q.s. | q.s. |
| Perfume | q.s. | q.s. | q.s. | q.s. |
| Feel | | | | |
| Spread | | | | |

As is apparent from the results shown in Tables 27 and 28, the foundations of the Examples have very good feel and good spread at the time of application because the amphoteric urethane resin and silicone polymer are used in combination.

To the contrary, the foundation of the Comparative Example has good feel because the amphoteric urethane resin is used, but is inferior in spread at the time of application.

As described above, according to the cosmetics of the present invention, the amphoteric urethane resin and silicone polymer cause micro phase separation and the silicone polymer is unevenly distributed on the surface, thereby making it possible to provide the surface with the smoothness. As a result, the cosmetics are superior in spread at the time of application without impairing the touch when using the amphoteric urethane resin. The cosmetics of the present invention exhibit the excellent water resistance to neutral water as a result of ion bond(s) between the carboxyl group(s) and the tertiary amino group(s), while they exhibit excellent cleansing properties to shampoo as a result of the debonding of ions. Furthermore, the cationic tertiary amino group in the amphoteric urethane resin interacts with the surface of negatively charged hairs to exhibit good adhesion.

When using an aqueous solution or a water dispersion of a silicone polymer as the silicone polymer, the compatibility with the amphoteric urethane resin is enhanced to some degree, thereby making it possible to prepare a cosmetic having good stability.

When structural units derived from ethylene oxide, as a nonionic hydrophilic component, is introduced into the structure of the amphoteric urethane resin, sufficient hydrophilicity is obtained and the hair washability are particularly improved when using as the hair cosmetic.

When a polysiloxane bond(s) is/are introduced into the structure of the above amphoteric urethane resin, the touch is particularly improved furthermore when using as the hair cosmetic.

What is claimed is:

1. A cosmetic composition comprising an amphoteric urethane resin having at least one carboxyl group and at least one tertiary amino group in a molecule, and silicone polymer.

2. The cosmetic according to claim 1, wherein said silicone polymer is a nonionic silicone polymer.

3. The cosmetic according to claim 1, wherein said silicone polymer is a polyether-modified silicone polymer.

4. The cosmetic according to claim 1, wherein said silicone polymer is a phenyl-modified silicone polymer.

5. The cosmetic according to claim 1, wherein said silicone polymer is an amino-modified silicone polymer.

6. The cosmetic according to claim 1, wherein said silicone polymer is an alkyl-modified silicone polymer.

7. The cosmetic according to claim 1, wherein said silicone polymer is an alkoxy-modified silicone polymer.

8. The cosmetic according to claim 1, wherein said silicone polymer is a cyclic silicone polymer.

9. The cosmetic according to claim 1, wherein said silicone polymer is in the form of an aqueous solution.

10. The cosmetic according to claim 1, wherein said silicone polymer is in the form of a water dispersion.

11. The cosmetic according to claim 1, wherein said amphoteric urethane resin has at least one structural unit derived from ethylene oxide in its structure.

12. The cosmetic according to claim 1, wherein said amphoteric urethane resin has at least one polysiloxane bond in its structure.

13. The cosmetic according to claim 1, wherein said amphoteric urethane resin is in the form of an aqueous solution.

14. The cosmetic according to claim 1, which is selected from the group consisting of a hair cosmetic, a skin care cosmetic and a make-up cosmetic.

* * * * *